United States Patent
Rosenberg et al.

(10) Patent No.: US 7,037,288 B2
(45) Date of Patent: May 2, 2006

(54) ANTI-BLOCK CATHETER

(75) Inventors: Meir Rosenberg, Newton, MA (US); Pierre Ostiguy, Hampshire, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 380 days.

(21) Appl. No.: 10/047,079

(22) Filed: Jan. 14, 2002

(65) Prior Publication Data

US 2003/0135147 A1     Jul. 17, 2003

(51) Int. Cl.
    *A61M 5/00*     (2006.01)
(52) U.S. Cl. ................. 604/8; 604/7; 604/264
(58) Field of Classification Search ........... 604/8–10, 604/264, 523, 525, 526, 530, 533, 534, 537, 604/43, 6.16, 246, 247, 27, 317; 600/29; 623/1, 1.22; 606/153
    See application file for complete search history.

(56) References Cited

U.S. PATENT DOCUMENTS

| | | | |
|---|---|---|---|
| 2,450,217 A * | 9/1948 | Alcorn | 604/93.01 |
| 3,815,608 A * | 6/1974 | Spinosa et al. | 604/105 |
| 4,215,695 A | 8/1980 | Spitz et al. | |
| 4,578,057 A | 3/1986 | Sussman | |
| 4,655,745 A | 4/1987 | Corbett | |
| 4,692,155 A | 9/1987 | Zimmer | |
| 4,767,400 A | 8/1988 | Miller et al. | |
| 4,950,232 A * | 8/1990 | Ruzicka et al. | 604/43 |
| 5,098,411 A | 3/1992 | Watson et al. | |
| 5,141,502 A * | 8/1992 | Macaluso, Jr. | 604/528 |
| 5,209,723 A * | 5/1993 | Twardowski et al. | 604/43 |

(Continued)

FOREIGN PATENT DOCUMENTS

EP     0 963 764 A1     12/1999

(Continued)

OTHER PUBLICATIONS

Phoenix Anti-Blok "*Catheter-Reservoir*" (*For CSF Shunting*); Internet Site Address: http://www.shunt.com/biomedical/instructions/NS/AntiBlokCR.htm.

*Primary Examiner*—Patricia Bianco
*Assistant Examiner*—Leslie R. Deak
(74) *Attorney, Agent, or Firm*—Nutter, McClennen & Fish, LLP

(57) ABSTRACT

An implantable fluid management device includes a catheter with an elongate proximal portion, a flexible distal portion, and a fluid passageway flowing therethrough. The distal portion includes a coil-shaped portion that defines a spiral having at least one turn. The distal portion of the catheter includes at least one pore in fluid communication with the fluid passageway of the catheter, which is located on an internal portion of the spiral. The positioning of the pore(s) on the internal portion of the spiral protects the pore(s) from obstruction or occlusion caused by tissue growing into or around the catheter.

17 Claims, 5 Drawing Sheets

U.S. PATENT DOCUMENTS

| | | |
|---|---|---|
| 5,405,316 A | 4/1995 | Magram |
| 5,514,176 A * | 5/1996 | Bosley, Jr. ................. 623/1.15 |
| 5,531,673 A | 7/1996 | Helenowski |
| 5,536,274 A * | 7/1996 | Neuss ....................... 623/1.22 |
| 5,897,528 A | 4/1999 | Schultz |
| 5,913,852 A | 6/1999 | Magram |
| 5,941,823 A | 8/1999 | Chait |
| 6,013,051 A | 1/2000 | Nelson |
| 6,595,966 B1 * | 7/2003 | Davey et al. ............... 604/264 |
| 6,620,202 B1 * | 9/2003 | Bottcher et al. ........... 623/23.7 |
| 6,676,623 B1 * | 1/2004 | Whitmore, III ................ 604/8 |
| 6,743,198 B1 * | 6/2004 | Tihon ........................ 604/104 |

FOREIGN PATENT DOCUMENTS

| | | |
|---|---|---|
| FR | 2 785 815 A1 | 5/2000 |
| WO | WO 89/02290 | 3/1989 |
| WO | WO 98/11934 | 3/1998 |

* cited by examiner

ANTI-BLOCK CATHETER

FIELD OF THE INVENTION

The present invention relates generally to a fluid management device that minimizes the risk of blockage or obstruction of the catheter pores, and more particularly, to a fluid management device with a catheter that includes a coiled portion having pores on the internal surface of the coil.

BACKGROUND OF THE INVENTION

Hydrocephalus is a neurological condition that is caused by the abnormal accumulation of cerebrospinal fluid (CSF) within the ventricles, or cavities, of the brain. CSF is a clear, colorless fluid that is primarily produced by the choroid plexus and surrounds the brain and spinal cord. CSF constantly circulates through the ventricular system of the brain and is ultimately absorbed into the bloodstream. CSF aids in the protection of the brain and spinal cord. Because CSF keeps the brain and spinal cord buoyant, it acts as a protective cushion or "shock absorber" to prevent injuries to the central nervous system.

Hydrocephalus, which affects children and adults, arises when the normal drainage of CSF in the brain is blocked in some way. Such blockage can be caused by a number of factors, including, for example, genetic predisposition, intraventricular or intracranial hemorrhage, infections such as meningitis, head trauma, or the like. Blockage of the flow of CSF consequently creates an imbalance between the amount of CSF produced by the choroid plexus and the rate at which CSF is absorbed into the bloodstream, thereby increasing pressure on the brain, which causes the ventricles to enlarge.

Hydrocephalus is most often treated by surgically inserting a shunt system that diverts the flow of CSF from the ventricle to another area of the body where the CSF can be absorbed as part of the circulatory system. Shunt systems come in a variety of models, and typically share similar functional components. These components include a ventricular catheter which is introduced through a burr hole in the skull and implanted in the patient's ventricle, a drainage catheter that carries the CSF to its ultimate drainage site, and optionally a flow-control mechanism, e.g., shunt valve, that regulates the one-way flow of CSF from the ventricle to the drainage site to maintain normal pressure within the ventricles. The ventricular catheter typically contains multiple holes or pores positioned along the length of the ventricular catheter to allow the CSF to enter into the shunt system. To facilitate catheter insertion, a removable rigid stylet, situated within the lumen of the ventricular catheter, is used to direct the catheter toward the desired targeted location. Alternatively, or in addition, blunt tip brain cannulas and peel-away sheaths have been used to aid placement of the catheters.

Shunting is considered one of the basic neurosurgical procedures, yet it has the highest complication rate. The most common complication with shunting is obstruction of the system. Although obstruction or clogging may occur at any point along the shunt system, it most frequently occurs at the ventricular end of the shunt system. While there are several ways that the ventricular catheter may become blocked or clogged, obstruction is typically caused by growth of tissue, such as the choroid plexus, around the catheter and into the pores. The pores of the ventricular catheter can also be obstructed by debris, bacteria, or blood clogged in the pores of the catheter. Additionally, problems with the ventricular catheter can arise from overdrainage of the CSF, which can cause the ventricle walls to collapse upon the catheter and block the pores in the catheter wall, thereby preventing CSF drainage.

Some of these problems can be treated by backflushing, which is a process that uses the CSF present in the shunt system to remove the obstructing matter. This process can be ineffective, however, due to the small size of the pores of the ventricular catheter and due to the small amount of flushing liquid available in the shunt system. Other shunt systems have been designed to include a mechanism for flushing the shunt system. For example, some shunt systems include a pumping device within the system which causes fluid in the system to flow with considerable pressure and velocity, thereby flushing the system. As with the process of backflushing, using a built-in mechanism to flush the shunt system can also fail to remove the obstruction due to factors such as the size of the pores and the degree and extent to which the pores have been clogged.

Occluded ventricular catheters can also be repaired by cauterizing the catheter to remove blocking tissue, thereby reopening existing pores that have become occluded. Alternatively, new pores can be created in the catheter. These repairs, however, may be incapable of removing obstructions from the ventricular catheter depending on the location of the clogged pores. Additionally, the extent of tissue growth into and around the catheter can also preclude the creation of additional pores, for example, in situations where the tissue growth covers a substantial portion of the ventricular catheter. Another disadvantage of creating new apertures to repair an occluded ventricular catheter is that this method fails to prevent or reduce the risk of repeated obstructions.

Because attempts at flushing or repairing a blocked ventricular catheter are often futile and ineffective, occlusion is more often treated by replacing the catheter. Although this can be accomplished by simply removing the obstructed catheter from the ventricle, the growth of the choroid plexus and other tissues around the catheter and into the pores can hinder removal and replacement of the catheter. Care must be exercised to avoid damage to the choroid plexus, which can cause severe injury to the patient, such as, for example, hemorrhaging. Not only do these procedures pose a significant risk of injury to the patient, they can also be very costly, especially when shunt obstruction is a recurring problem.

Accordingly, there exists a need for a shunt system that minimizes or eliminates the risk of blockage or obstruction of the catheter pores, and reduces the need for repeated repair and/or replacement.

SUMMARY OF THE INVENTION

The present invention overcomes the disadvantages that are inherent in prior art fluid management systems by providing an implantable catheter with a coiled end that has a pore or pores, located on the inwardly facing surface of the coil. The fluid management device of the present invention includes a conduit with a proximal portion that is elongate and substantially cylindrical, a distal portion that can assume the shape of a coil with at least one revolution, and a fluid passageway extending between the distal and proximal portions. According to the present invention, the coiled shape of the distal portion may also contain more than one revolution. When tensile forces are applied to the catheter, the revolution or revolutions of the coiled distal portion are removed, and both the proximal and distal portions of the conduit are substantially straight. Upon removal of the tensile forces, the distal portion once again assumes its coil-like shape. The coils of the catheter are preferably close together to minimize the growth of the choroid plexus or other tissues at the site of implantation into and around the catheter.

Fluid enters the fluid passageway of the conduit through one or more openings, also known as pores, in the distal, coiled portion of the conduit. At least one pore is located on the internal surface of the coils of the catheter in the present invention. Thus, at least one pore is not adjacent to the tissue at the site of implantation and is thereby protected from tissue by the revolutions of the coil. In the present invention, the conduit can have virtually any number of pores, and the pores may have virtually any size or shape.

Further features of the invention, its nature and various advantages, will be more apparent from the accompanying drawings and the following detailed description of the drawings and the preferred embodiments.

DETAILED DESCRIPTION OF THE INVENTION

The implantable fluid management device of the present invention facilitates the removal or introduction of fluid to a treatment site. By way of example, a distal portion of the device can be implanted in the ventricle of the brain to drain excess fluid from within the ventricles, directing it to another site in the patient's body. The fluid management device of the present invention is advantageous as its construction enables fluid to be drained while minimizing the risk that the drainage catheter will be blocked or occluded.

Figure 1:
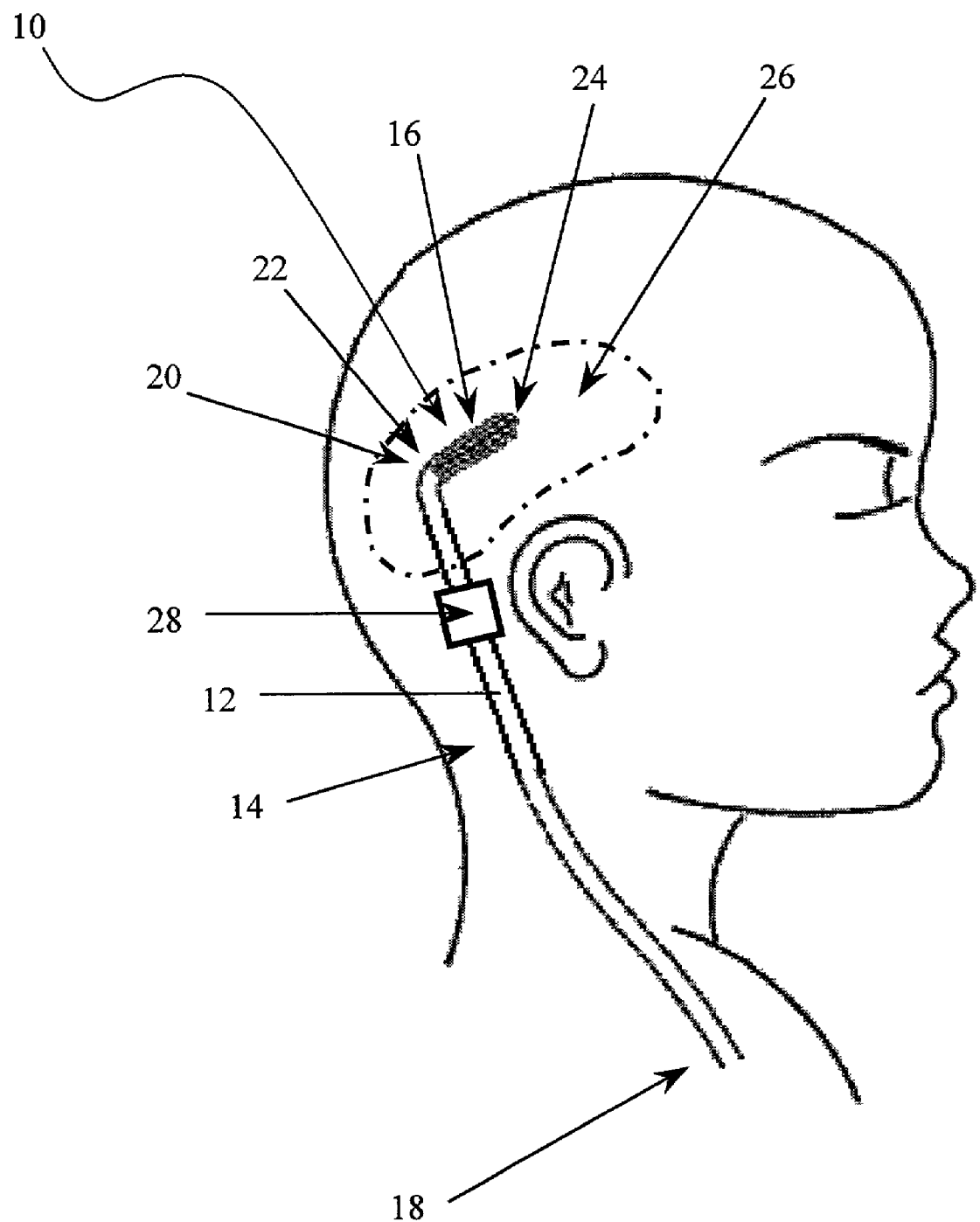
FIG. 1 is a semi-transparent perspective view illustrating a fluid management device of the present invention implanted in a subject.

As shown in FIG. 1, the implantable fluid management device 10 includes a catheter 12 having proximal and distal portions 14, 16 with a fluid passageway extending therebetween. The proximal portion 14 of the catheter 12 has a first, open end 18 and a transition end 20 and a lumen 30 (FIGS. 2A, 3A and 3B) connecting the two ends. The distal portion 16 of the catheter 12 is defined by an outer wall 44 (FIGS. 4 and 5) and has a first, connecting end 22 and a second, distal-most end 24 and a lumen 40 (FIGS. 3B and 4) extending therebetween. The distal portion 16 of the catheter 12 further includes at least one fluid entry port 42 (FIG. 4) disposed in the outer wall 44 of the catheter 12 and in fluid communication with the inner lumen 40 of the distal portion 16. Referring to FIGS. 1–3A and 4, the normal shape of the distal portion 16 of the catheter 12 is a coil-like shape that defines a spiral structure having at least one revolution. Preferably, the fluid entry port or pore 42 is disposed on an internal portion 48 (FIGS. 4 and 5) of the spiral or coil.

In use, the distal portion 16 of the catheter 12, and at least a portion of the proximal portion 14, is implanted at a site within a patient's body, e.g., the ventricle of the brain 26, from which fluid is to be drained. Fluid is then drained from the ventricles 26 and directed through the catheter 12 to the first, open end 18 from which it can be discharged into another part of the patient's body, e.g., the peritoneum or the atrium of the heart, where it is absorbed into the bloodstream. The first, open end 18 can also be mated to a shunt valve 28 that is effective to regulate the flow of fluid through the fluid management device 10. In a further embodiment, the fluid management device 10 can be used to deliver fluid and/or drugs to a treatment site and, accordingly, the first, open end 18 can be mated to a source of fluid and/or drugs.

Figure 2A:
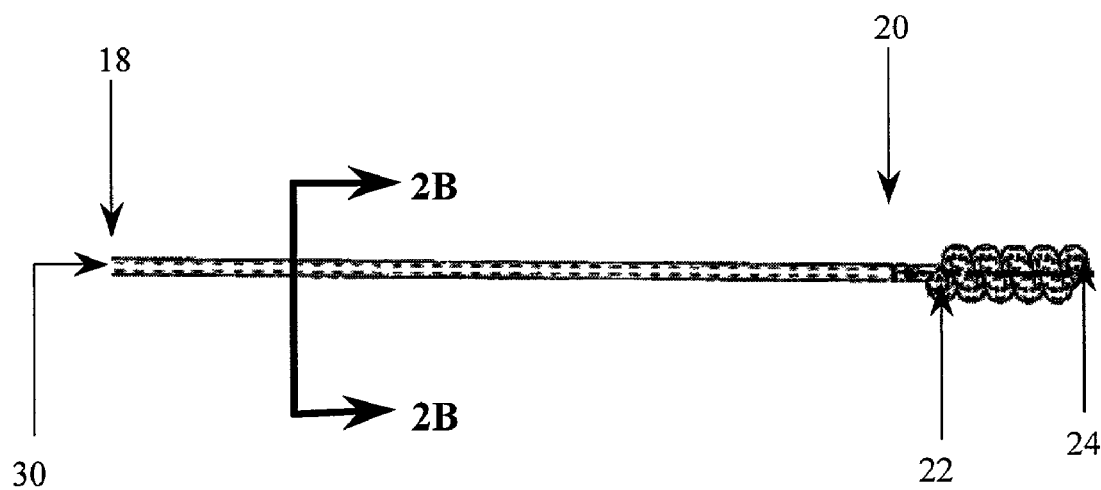
FIG. 2A is a perspective view of the catheter of the fluid management device of FIG. 1, according to one embodiment of the present invention.
Figure 2B:
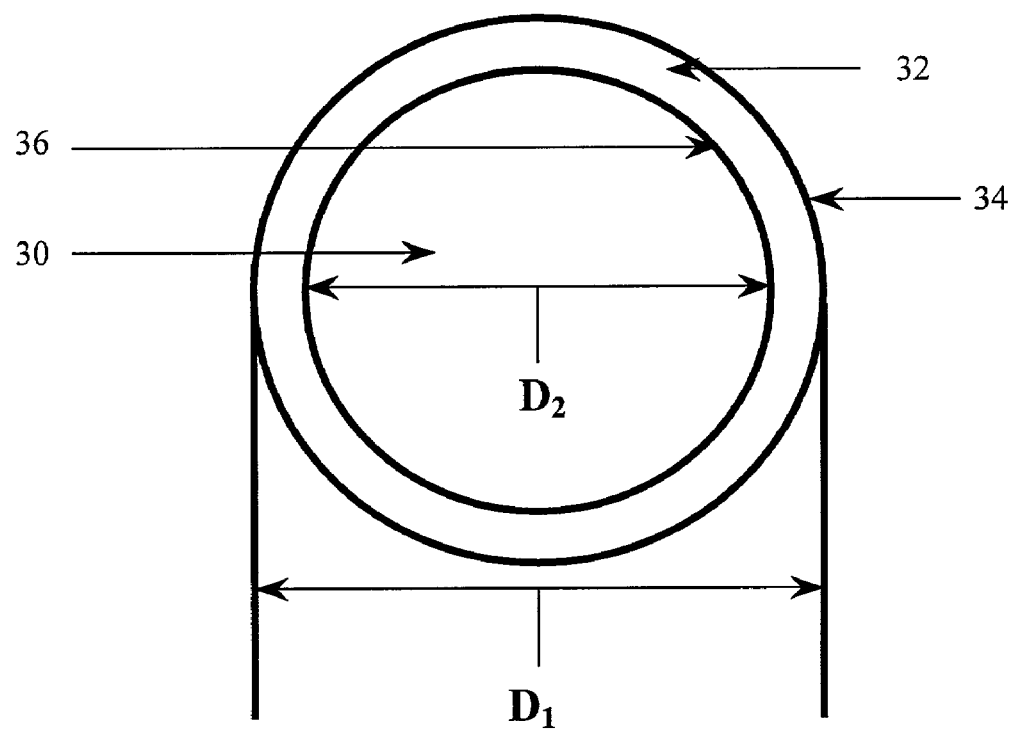
FIG. 2B is an enlarged cross-sectional view of the proximal portion of the catheter along line 2B—2B of FIG. 2A.
Figure 3A:
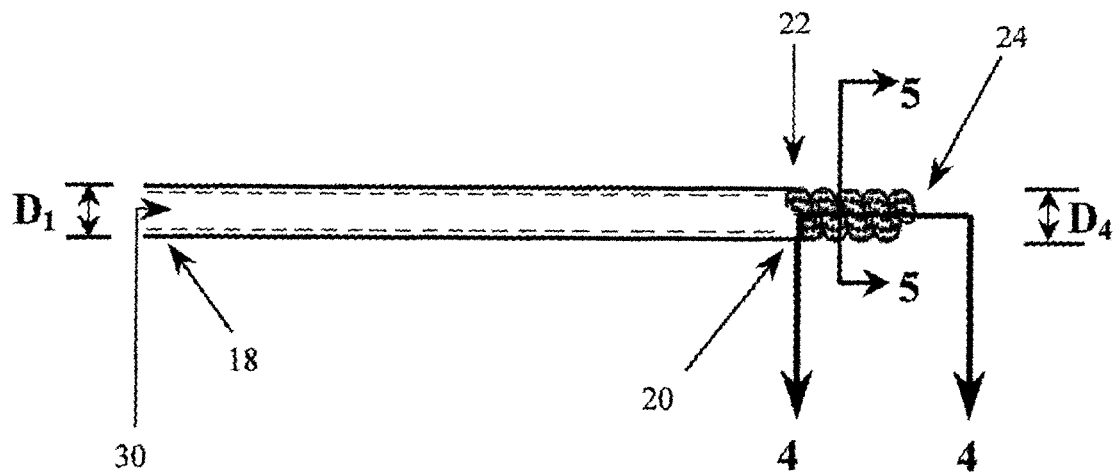
FIG. 3A is a perspective view of the catheter of the fluid management device of FIG. 1, according to another embodiment of the present invention.
Figure 3B:
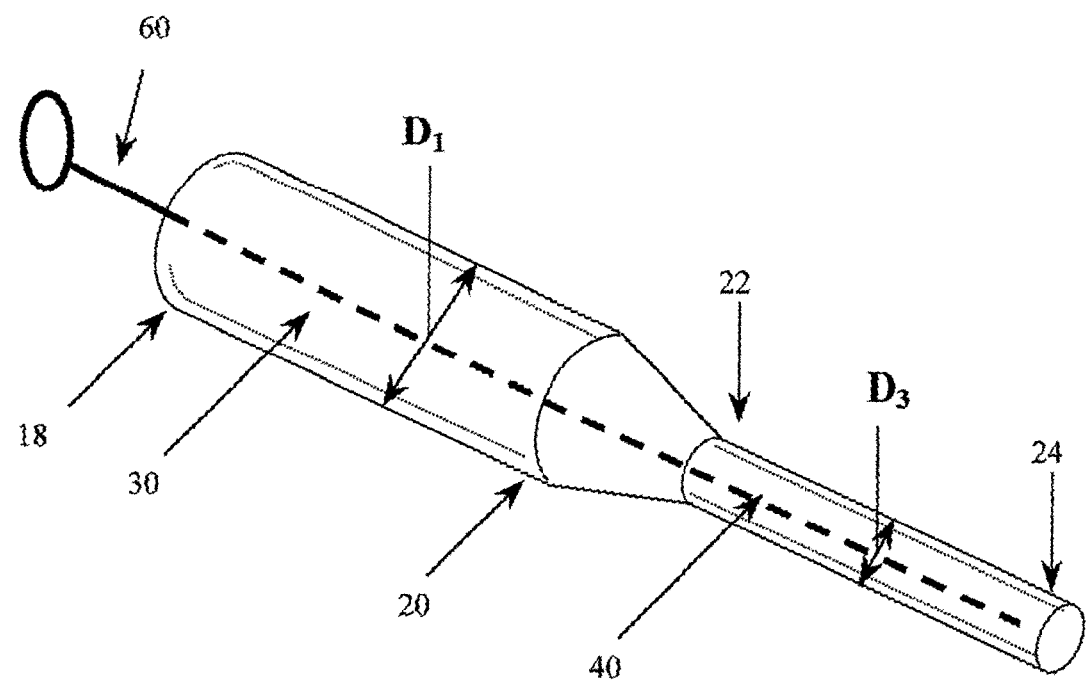
FIG. 3B is a perspective view of the catheter of FIG. 3A including a rigid stylet inserted therein, according to the present invention.

The proximal portion 14 of the catheter 12, which is illustrated in more detail in FIGS. 2A through 3B, can have virtually any shape, but is preferably an elongate, substantially cylindrical member. Referring to FIGS. 2 through 3B, the proximal portion 14 is defined by an outer wall 32 and has an inner lumen 30 extending between a first, open end 18 and a transition end 20. The first, open end 18 of the proximal portion 14 is open and in fluid communication with the inner lumen 30 to allow fluid to flow through the proximal portion 14. The transition end 20 of the proximal portion 14 is attached to the distal portion 16 of the catheter 12, as shown in FIGS. 2A, 3A and 3B.

Referring to FIGS. 2B through 3B, the proximal portion 14 of the catheter 12 has an outer diameter $D_1$. The term "outer diameter $D_1$ of the proximal portion 14," as used herein, is defined as the distance between any two points, located on the external surface 34 (FIG. 2B) of the outer wall 32, that are connected by a straight line passing through the center of the proximal portion 14. The inner lumen 30 of the proximal portion 14 has a lumen diameter $D_2$, as shown in FIG. 2B. The term "lumen diameter $D_2$ of the proximal portion 14," as used herein, is defined as the distance between any two points, located on the internal surface 36 of the outer wall 32, that are connected by a straight line passing through the center of the proximal portion 14.

The proximal portion 14 of the catheter 12 can have virtually any length, but preferably, the length of the proximal portion 14 is in the range of about 30 to 100 mm. As shown in FIGS. 2A through 3B, the outer diameter $D_1$ of the proximal portion 14 of the catheter 12 can vary, but preferably, the outer diameter is sized according to the proportions of the target implantation site. More preferably, the outer diameter $D_1$ of the proximal portion 14 of the catheter 12 is in the range of about 2 to 4 mm. The lumen diameter $D_2$ of the proximal portion 14 of the catheter 12 can also vary, but preferably, the lumen diameter $D_2$ is sufficient to allow fluid to flow through the inner lumen 30 of the proximal portion 14. More preferably, the lumen diameter $D_2$ is in the range of about 0.5 to 2 mm.

Figure 4:
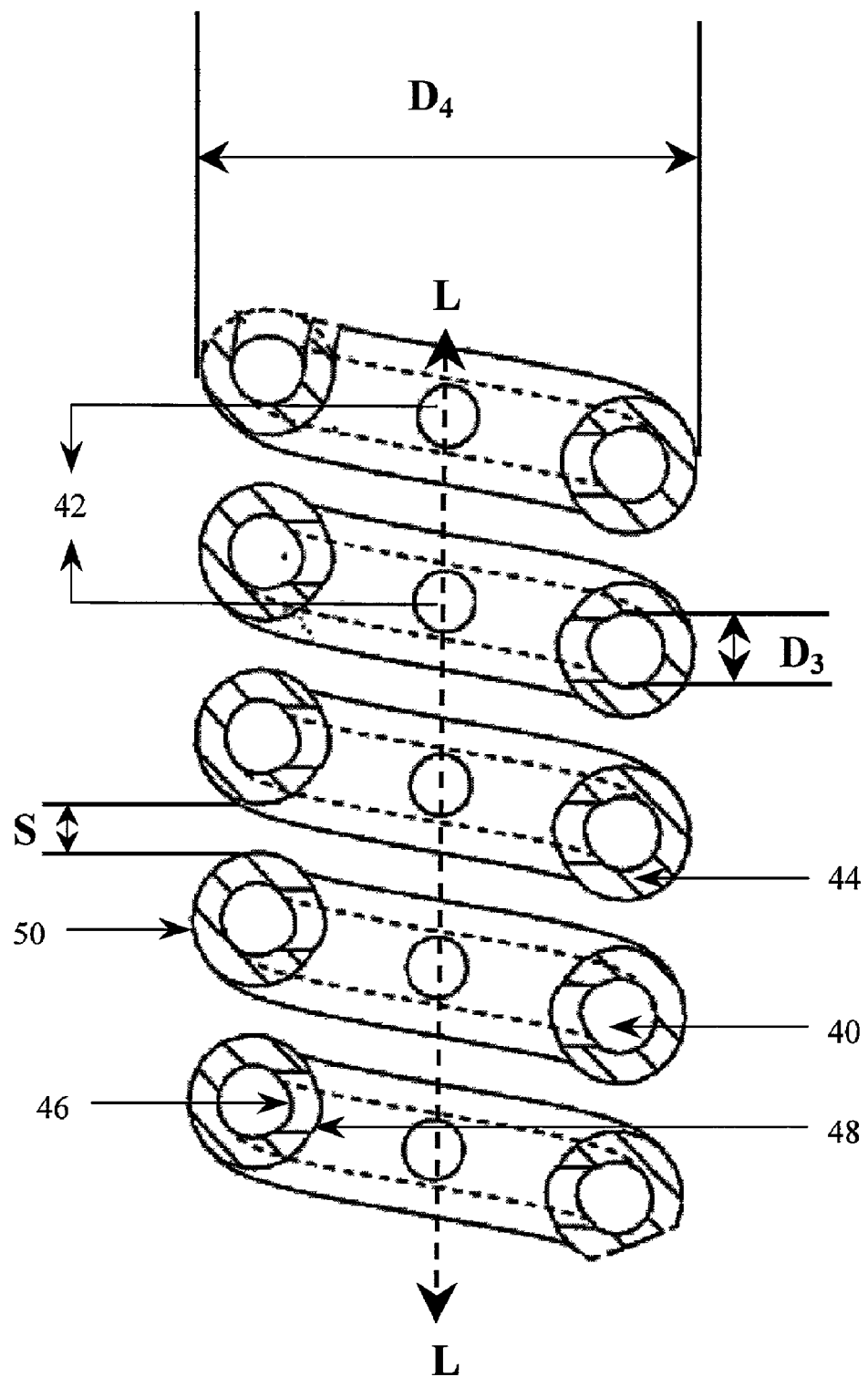
FIG. 4 is an enlarged cross-sectional view of the distal portion of the catheter along line 4—4 of FIG. 3A.

Referring to FIGS. 2A through 3B, the distal portion 16 of the catheter 12 has a first, connecting end 22 that is open and in fluid communication with the inner lumen 30 of the proximal portion 14 to allow fluid to flow into and out of the distal portion 16. The second, distal-most end 24 of the distal portion 16 can be open and in fluid communication with the inner lumen 40 of the distal portion 16. Alternatively, the second, distal-most end 24 can be closed or sealed to prevent fluid from flowing therethrough. The inner lumen 40 extending between the first, connecting end 22 and the second, distal-most end 24 can have virtually any shape, but is preferably substantially cylindrical, as shown in FIG. 4. The inner lumen 40 of the distal portion has a lumen diameter $D_3$. The term "lumen diameter $D_3$ of the distal portion 16," as used herein, is defined as the distance between any two points, located on the internal surface 46 of the outer wall 44, that are connected by a straight line passing through the center of the inner lumen 40 of the distal portion 16.

Figure 5:
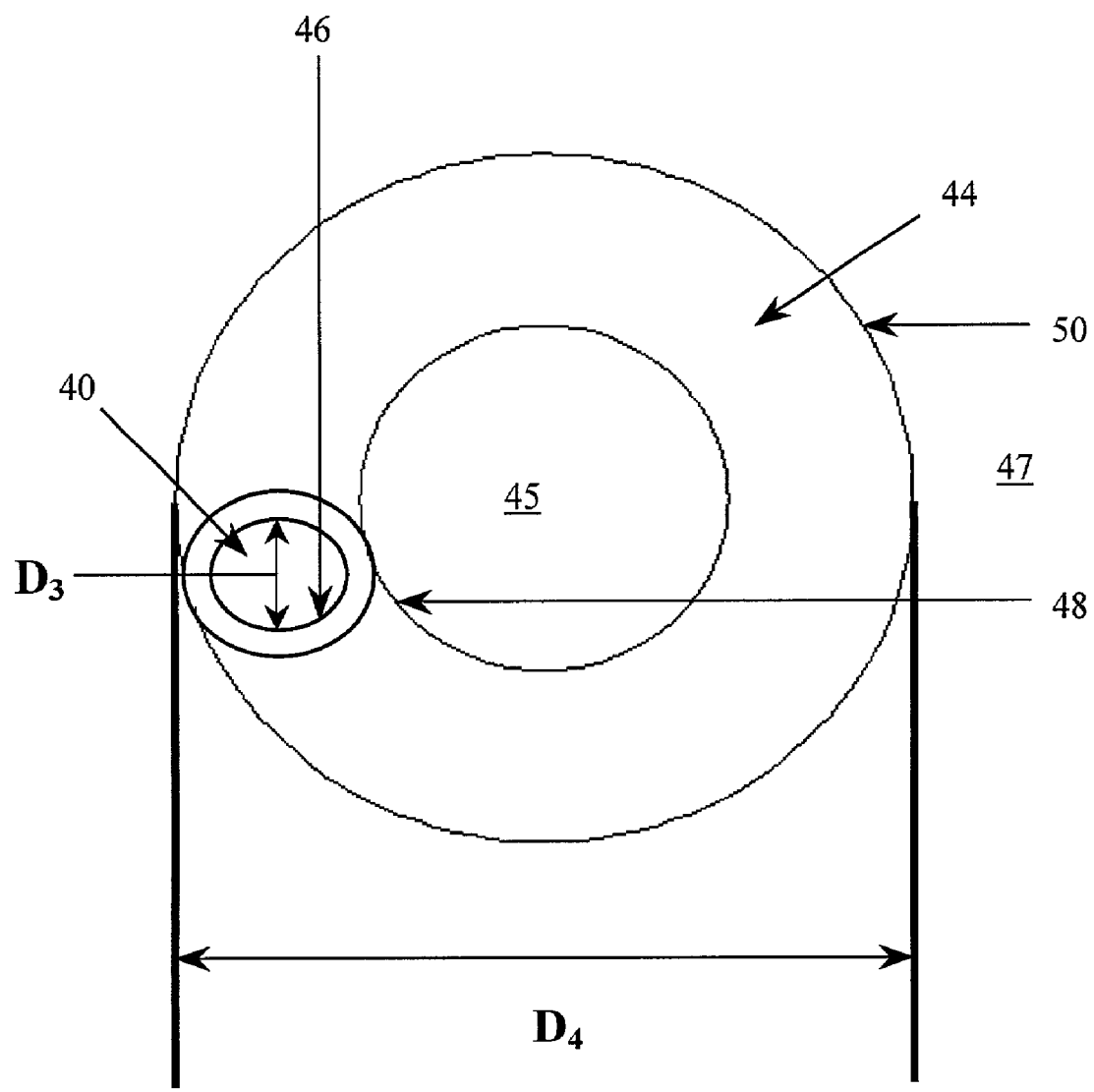
FIG. 5 is an enlarged cross-sectional view of the distal portion of the catheter along line 5—5 of FIG. 3A.

Referring to FIGS. 2A through 4, the distal portion 16 of the catheter 12 can have virtually any shape, but preferably, the distal portion 16 is an elongate, substantially cylindrical member that has been biased or preconfigured coiled shape defining a spiral. The spiral or coiled shape of the distal portion 16 defines a region 45 (FIG. 5) that is internal with respect to the spiral or coil. Moreover, the distal portion 16 has an internal coil surface 48 and an external coil surface 50, as shown in FIGS. 4 and 5. The internal coil surface 48, as used herein, refers to the coil surface that faces the region 45 internal to and surrounded by the spiral or coiled shape of the distal portion 16. The external coil surface 50, as used herein, refers to the coil surface that faces an outer region 47 (FIG. 5) that is opposed to region 45.

The spiral or coiled shape of the distal portion 16 of the catheter 12 can have virtually any number of turns. The term "turn" as used herein is defined as one rotation around a coil, i.e., starting at any point along the coil and winding around the central, longitudinal axis (L) of the coil for 360°. Preferably, the distal portion 16 of the catheter 12 has more than one turn, and more preferably, the number of turns is in the range of about 1 to 10. By way of non-limiting example, FIG. 2A illustrates an embodiment in which the spiral has five turns. Referring to FIG. 4, the spacing S between each successive turn of the spiral or coiled shape can vary, but preferably, the spacing is sufficient to prevent tissue from growing between successive turns of the spiral or coiled shape. More preferably, the spacing S between successive turns is in the range of about 0 to 2 mm.

Referring to FIGS. 3A, 4 and 5, the spiral or coiled shape of the distal portion 16 has an outer diameter $D_4$. The outer diameter $D_4$ of spiral or coiled shape of the distal portion 16, as used herein, refers to the distance between any two points on the external coil surface 50 that are connected by a straight line passing through the central, longitudinal axis of the spiral or coiled shape of the distal portion 16. A person having ordinary skill in the art will appreciate that the size of the outer diameter $D_4$ of the spiral or coiled shape of the distal portion 16 can vary according to its intended application. By way of example, a catheter 12 designed for use in an infant or child can have a smaller outer diameter $D_4$ of the spiral or coiled shape of the distal portion 16 than a catheter 12 designed for use in an adult. Preferably, the outer diameter $D_4$ of the spiral or coiled shape of the distal portion 16 is substantially equal to, or not more than four times greater than the outer diameter $D_1$ (FIG. 2B through 3B) of the proximal portion 14. More preferably, the outer diameter $D_4$ of the coiled shape is in the range of about 4 to 9 mm. One of ordinary skill in the art will appreciate that it is advantageous to have a catheter 12 where the outer diameter $D_4$ of the coiled shape of the distal portion 16 is substantially the same size as, or not much larger than, the outer diameter $D_1$ of the proximal portion 14 in order to minimize any damage that may result during implantation of the fluid management device 10.

Referring to FIG. 4, the distal portion 16 of the catheter 12 further includes at least one fluid entry port or pore 42, which extends through the outer wall 44 of the distal portion 16 and is in fluid communication with the inner lumen 40 of the distal portion 16. Preferably, the pore(s) is located on the internal coil surface 48 such that it is sheltered or protected by the turns of the spiral or coiled shape of the distal portion 16. The internal coil surface 48 can contain any number of fluid entry ports 42, but preferably the number of fluid entry ports 42 located on the internal coil surface 48 is in the range of about 4 to 40.

A person having ordinary skill in the art will appreciate that each fluid entry port 42 can have virtually any size, shape or position on the internal coil surface 48. The size of each fluid entry port can vary, but preferably, the area of each fluid entry port 42 is in the range of about 0.05 to 1 mm². Each fluid entry port 42 can have virtually any shape, such as for example, circular, ovular, rectangular, square or any combination thereof. Preferably, each fluid entry port has a circular shape. Each fluid entry port 42 can be located virtually anywhere along the internal coil surface 48, and the spacing between successive fluid entry ports 42 can vary. For example, the spacing between each fluid entry port 42 can be uniform, erratic or a combination of both. By way of non-limiting example, FIG. 4 illustrates an embodiment having uniformly-spaced fluid entry ports 42 that are aligned along a longitudinal axis L of the spiral or coiled shape of the distal portion 16.

In one embodiment of the present invention, the proximal and distal portions 14, 16 of the catheter 12 may be integrally formed. Alternatively, the proximal and distal portions 14, 16 may comprise two separate members that have been mated together. A variety of mating techniques known to those having ordinary skill in the art can be used to couple the proximal and distal portions 14, 16 of the catheter 12. By way of non-limiting example, the distal portion 16 can be welded, ultrasonically bonded, adhesively attached or mechanically mated to the proximal portion of the catheter 12.

The proximal and distal portions 14, 16 of the catheter 12 can be made from any biologically compatible material. Preferably, at least the distal portion 16 of the catheter 12 is constructed from a flexible material that is biased or preconfigured to a coiled shape, such as for example, silicone, silicone-like materials, shape memory materials, polyurethane or barium sulfate loaded polymers to enable X-ray detection. In one embodiment, at least the distal portion 16 of the catheter 12 can be constructed from a shape-memory material, or alternatively, at least the distal portion 16 of the catheter 12 can contain a shape-memory material embedded in the outer wall 44.

In use, the distal portion 16 of the catheter 12 can be transferable between its first or normal condition in which it assumes a spiral or coiled shape shown in FIG. 3A, and a second, substantially elongate condition shown in FIG. 3B. The ability of the distal portion 16 to transform between these two conditions facilitates insertion of the catheter 12 into a treatment site as well as effective performance. In one embodiment, a catheter 12 containing or made of a shape memory material, such as for example, a shape memory grade polyurethane, is provided in a substantially straightened or elongate condition, and the catheter is implanted in this condition. Once the catheter 12 is in the presence of an external stimulus, such as for example, body heat or bodily fluid, the distal portion 16 of the catheter 12 will assume its normal spiral or coiled shape, as shown in FIGS. 2A and 3A. Alternatively, the catheter 12 can be inserted into a patient after a stylet 60 (FIG. 3B), which is effective to provide rigidity to the catheter 12, is inserted into the fluid management device 10 through the first, open end 18 of the proximal portion 14 of the catheter 12. The stylet 60 can be extended through the proximal and distal portions 14, 16 of the catheter 12, thereby causing the distal portion 16 of the catheter 12 to assume the substantially elongate position shown in FIG. 3B. Once the catheter 12 is implanted at the treatment site, the stylet 60 can be removed. Upon removal of the stylet 60, the distal portion 16 of the catheter 12 again assumes its normal spiral or coiled shape shown in FIGS. 2A, 3A and 4.

In yet another embodiment, the catheter 12 can be placed in a sheath (not shown) prior to insertion within a patient. The sheath, which can be, for example, a plastic tube, is effective to cause the distal portion 16 of the catheter 12 to assume the substantially elongate position shown in FIG. 3B. The sheath may be placed around the body of the catheter 12 during catheter 12 production, or alternatively, the sheath may be manually applied to the body of the catheter 12 at some point prior to insertion. After the catheter 12 has been implanted at the treatment site, the sheath may be removed. Upon removal of the sheath, the distal portion 16 of the catheter 12 again assumes its normal spiral or coiled shape, as shown in FIGS. 2A, 3A and 4.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

The invention claimed is:

1. An implantable fluid management device, comprising:
    a catheter having a proximal portion, a distal portion and an outer wall that defines an inner lumen extending between the proximal and distal portions;
    a coil-shaped region formed on the distal portion and having an outer diameter, measured across the coil-shaped region, that is substantially equal to an outer diameter of the proximal portion of the catheter, the coil-shaped region forming a spiral having successive turns that are space apart from one another; and
    at least one fluid entry port formed on an internal portion of the coil-shaped region and in fluid communication with the inner lumen of the catheter.

2. The device of claim 1, wherein the coil-shaped region has an outer diameter, measured across the spiral, that is less than about ten millimeters.

3. The device of claim 1, wherein the length of the spiral formed by the coil-shaped region of the catheter, measured from a first end to a second end thereof, is in the range of about 30 to 100 mm.

4. The device of claim 3, wherein the spiral formed by the coil-shaped region of the catheter has about 1 to 10 turns.

5. The device of claim 1, further comprising a fluid entry port formed at a distal-moat end of the distal portion of the catheter and in fluid communication with the inner lumen of the catheter.

6. The device of claim 1, wherein the number of the at least one fluid entry port is in the range of about 1 to 40.

7. The device of claim 1, wherein the shape of the at least one fluid entry port is selected from the group consisting of circular, oval, and a polygon.

8. The device of claim 1, wherein the catheter includes a plurality of fluid entry ports formed on an internal portion of the coil-shaped region, the fluid entry ports having a combination of varying shapes.

9. The device of claim 1, wherein an area of the at least one fluid entry port is in the range of about 0.05 to 1 mm$^2$.

10. The device of claim 1, wherein the catheter includes a plurality of fluid entry ports formed on an internal portion of the coil-shaped region, the fluid entry ports having a combination of varying areas.

11. The device of claim 1, wherein the coil-shaped portion of the distal portion of the catheter is constructed from a flexible material that is adapted to allow tensile forces to remove the spiral, and that is adapted to cause the spiral to return upon removal of the tensile forces.

12. The device of claim 11, wherein the coil-shaped portion of the catheter is constructed from a flexible material selected from the group consisting of silicone, silicone-like materials, shape memory materials, polyurethane, and barium sulfate loaded polymers.

13. The device of claim 12, wherein at least a portion of distal portion of the catheter is constructed from a shape memory material and exposure to an external stimulus causes the distal portion to form a spiral having at least one turn.

14. The device of claim 12, wherein at least a portion of the outer wall of the distal portion of the catheter contains a shape memory material therein and exposure to an external stimulus causes the distal portion to form a spiral having at least one turn.

15. The device of claim 1, wherein the distal portion and the proximal portion of the catheter comprise separate elements of the catheter, the distal portion being coupled to the proximal portion by a technique selected from the group consisting of welding, bonding, molding, adhesively attaching and mechanically mating.

16. An implantable fluid management device, comprising:
    a catheter having an inner lumen extending between proximal and distal ends;
    a coil-shaped region formed on the distal end of the catheter and having successive turns that are spaced apart from one another by a distance that is adapted to prevent tissue from growing into the coil-shaped region, the coil-shaped region having an outer diameter, measured across the coil-shaped region, that is substantially equal to an outer diameter of the catheter, the coil-shaped region further including at least one fluid entry port in communication with the inner lumen of the catheter and formed internal to the coil-shaped region such that the at least one fluid entry port is sheltered by the coil-shaped region.

17. The device of claim 16, wherein the distance between each successive turn of the coil-shaped region is in the range of about 0 to 2 mm.

* * * * *